United States Patent [19]

Gordon

[11] Patent Number: 5,157,024
[45] Date of Patent: Oct. 20, 1992

[54] METHOD OF ENHANCING THE ACTIVITY OF PHAGOCYTES INCLUDING MACROPHAGES, MODULATING THE CELLULAR OR HUMORAL IMMUNE RESPONSE, AND REDUCING THE ADVERSE EFFECTS OF STRESS IN WARM BLOODED ANIMALS

[75] Inventor: Paul Gordon, Chicago, Ill.

[73] Assignee: Strategic Medical Research Corporation, Greenwich, Conn.

[21] Appl. No.: 159,517

[22] Filed: Feb. 19, 1988

Related U.S. Application Data

[63] Continuation of Ser. No. 473,263, Mar. 14, 1983, abandoned, which is a continuation of Ser. No. 234,504, Feb. 17, 1981, abandoned, which is a continuation of Ser. No. 125,568, Feb. 28, 1980, abandoned, which is a continuation of Ser. No. 845,797, Oct. 16, 1977, abandoned.

[51] Int. Cl.$^5$ .............................................. A61K 31/70
[52] U.S. Cl. ........................................ 514/23; 514/25; 514/885; 514/889; 514/921; 536/17.4; 536/17.6; 536/17.9; 536/120
[58] Field of Search .................. 514/23, 25, 885, 889, 514/921; 536/17.4, 17.6, 17.9, 120

[56] References Cited

U.S. PATENT DOCUMENTS

| | | | |
|---|---|---|---|
| 3,939,145 | 2/1976 | Gordon | 424/180 |
| 3,939,146 | 2/1976 | Gordon | 424/180 |
| 4,017,608 | 4/1977 | Gordon | 424/180 |

OTHER PUBLICATIONS

John W. Hadden et al., Int. J. Immuunopharmac., vol. 1, 1979, 17–27.
Christine J. Morrison et al., Antimicrobial Agents and Chemotherapy, Jul. 1984, pp. 74–77.
Vernoica Ruszala-Mallon et al., Int. J. Immuunopharmac., vol. 10, No. 5, 1988, pp. 497–510.
The Merck Manual of Diagnosis & Therapy, 13th Edition, pp. 1320–1331, 1344–1349 (1977).

*Primary Examiner*—Ronald W. Griffin
*Attorney, Agent, or Firm*—Finnegan, Henderson, Farabow, Garrett & Dunner

[57] ABSTRACT

In one variant, the invention provides a method of enhancing the activity of phagocytes including macrophages, and in a further variant, a method of modulating the cellular or humoral immune response to warm blooded animals. The invention also provides a method of reducing the adverse effects of stress in warm blooded animals. This is accomplished by administering an ethereally monosubstituted monosaccharide having the general formula $M_1$—O—Y, an ethereal monosubstitution of monosaccharide derivatives having the general formula $M_2$—O—Y, or pharmaceutically acceptable organic acid and inorganic acid salts thereof as defined hereinafter. In the first variant, the above substances are administered in an amount effective to enhance the microbicidal activity of phagocytes, including macrophages in a normal to depressed state of activation or macrophages already activated in response to infection. In the second variant, the above substances are administered in an amount to enhance the cellular or humoral immune response when the warm blooded animal has a normal or depressed cellular or humoral immune response system, or in an amount effective to reduce the cellular or humoral immune response when the warm blooded animal has a hypersensitive cellular or humoral immune response system. In the third variant, the above substances are administered in an amount effective to reduce the adverse effects of stress on the aforementioned defense mechanisms of warm blooded animals subjected to stress.

13 Claims, No Drawings

METHOD OF ENHANCING THE ACTIVITY OF PHAGOCYTES INCLUDING MACROPHAGES, MODULATING THE CELLULAR OR HUMORAL IMMUNE RESPONSE, AND REDUCING THE ADVERSE EFFECTS OF STRESS IN WARM BLOODED ANIMALS

This application is a continuation of application Ser. No. 06/473,263, filed Mar. 14, 1983, now abandoned, which was a continuation of application Ser. No. 06/234,504, filed Feb. 17, 1981, now abandoned, which was a continuation of application Ser. No. 06/125,568, filed Feb. 28, 1980, now abandoned, which was a continuation of application Ser. No. 05/845,797, filed Oct. 26, 1977, now abandoned.

THE BACKGROUND OF THE INVENTION

1. The Field of the Invention

The present invention is concerned with a method of enhancing the activity of phagocytes in warm blooded animals. The invention is also concerned with a method of modulating the cellular or humoral immune response system of a warm blooded animal and, in still another variant, with a method of reducing the adverse effects of stress on the foregoing defense mechanisms of warm blooded animals.

2. The Prior Art

The defense mechanisms of warm blooded animals providing non-specific resistance and/or cellular or humoral immunity to invading living disease producing micro-organisms, viruses and other pathogens are well known and are described in a large number of publications. Examples of publications which are especially pertinent include an article entitled "Secretory Function of Mononuclear Phagocytes," The American Journal of Pathology, Volume 83, Pages 396 et. seq., (1976); an article entitled "Regulation of Immunity and Inflammation by Mediators from Macrophages," The American Journal of Pathology, Volume 85, Pages 465 et. seq. (1976); an article entitled "Cytotoxic Macrophages: A Rapid Nonspecific Response to Viral Infection," The Journal of Immunology, Volume 117, Pages 2067 et. seq. (1976); and the various publications cited and referred to therein, all of which including the citations are incorporated herein by reference.

As is discussed in the aforementioned publications, it is generally accepted that a warm blooded animal's first line of defense against a cancer cell or against an invading microorganism, be it bacterium, fungus, protozoa, virus, or other pathogen, in the absence of previously acquired cellular or humoral immunity, involves non-specific cellular defense mechanisms. Prominent among these defending cells are the blood-borne and local or tissue phagocytes, including macrophages and their precursor monocytes, and phagocytes of a relatively short life span such as neutrophils, polymorphonuclear leukocytes or microphages.

Examples of other cells and substances involved in specific immunity include T-lymphocytes, B-lymphocytes and antibodies produced thereby. In the normal sequence of events, the non-specific phagocytes including macrophages in a highly cytotoxic activated state appear on the first day an animal is infected and increase until the second or third day of the infection. Specifically sensitized highly activated T-lymphocytes usually appear on the third day following infection, and increase in numbers until approximately the sixth day. Antibodies and other components of the humoral immune response system usually appear on the fourth day following infection and increase until approximately the eighth day.

The phagocytes and especially the monocyte macrophage system of cells perform other important functions in addition to the phagocytosis and destruction of invading microorganisms and cancer cells.

It is thought that two interrelated functions of macrophages in immunologic processes are to concentrate and remove antigen and to present certain substances for recognition to T-lymphocytes and/or B-lymphocytes. The association of an antigen with macrophages appears to be an early and important step in building up a complete immune response through the lymphocytes. The macrophages also secrete substances which have the capacity to enhance, reduce or otherwise change the response of the lymphocytes. The macrophages serve as the main effector cells and modulate the immune processes either up or down in accordance with their own state or degree of activation through interactions with the lymphocytes and especially with the T-lymphocytes.

The activity of macrophages may be modulated either up or down. Prior to infection of the warm blooded animal, they may exist in a normal, basal or depressed state of activation and in these states they do not have a pronounced modulating effect on the immune response system. The phagocytes and especially the macrophages, are capable of being activated when challenged by diverse invading microorganisms, by secretions from the T-lymphocytes, or by certain chemicals. The resulting activated macrophages are characterized by a markedly increased phagocytic activity, an increased content of acid hydrolyases, a more active metabolism, an increased microbicidal capacity, and a increased rate of secreting immunomodulating substances. The importance of the state of activation of the macrophages, as well as the importance of the state of activation of the components of the cellular and humoral immune response systems, are well known and recognized in this art and are described in the aforementioned publications. The capacity of compounds of the invention to enhance the microbicidal activity of macrophages that are at rest, that may be depressed by other drug therapies as adrenocorticosteroids, or that are already non-specifically activated in response to infection results from the special capacity of compounds of the invention to increase the generation of intracellular microbicidal enzymes and to increase the generation and efficiency of utilization of microbe-oxidizing substrates such as hydrogen peroxide, superoxide, etc. It is known that the phagocytes and especially the macrophages, T-lymphocytes, B-lymphocytes and other components of the cellular and humoral immune response systems must be stimulated in order to function most effectively and to provide optimum resistance to invading microorganisms and cancer cells. However, it is possible for the cellular and/or humoral immune response systems to become too highly activated due to a failure of feedback control as the generation of depressor T-cell signals or depressor macrophage signals. In this hypersensitive condition, the immune functions can be enhanced excessively for certain antigens, as in allergies such as hay fever and in autoimmune type diseases including rheumatoid arthritis and the like.

Immunity and inflammation are regulated by mediators from phagocytes and especially macrophages, and also by mediators from T-lymphocytes and other components of the cellular and/or humoral immune response systems. It has been established that certain cells emit positive control signals and enhance the activity of phagocytes and/or the immune responses, whereas still other cells emit negative control signals and decrease the activity of phagocytes and/or the immune responses. Thus, it is apparent that a method capable of modulating the activity of phagocytes and/or the cellular and/or humoral immune response systems within the ranges sufficiently high to assure adequate resistance to invading disease producing micro-organisms and cancer cells, and yet within ranges providing a sufficiently low state of activation to prevent or suppress diseases or conditions resulting from a hypersensitive cellular or humoral immune response system such as allergies and autoimmune diseases, would be of great benefit. However, an entirely satisfactory method was not available prior to the present invention whereby these desired benefits could be achieved with drugs which are non-toxic and free of side effects.

THE SUMMARY OF THE INVENTION INCLUDING CERTAIN OBJECTS THEREOF

The present invention provides a method of enhancing the microbicidal activity of phagocytes including macrophages in a normal to depressed state of activation or macrophages already activated in response to infection, and/or modulating the normal to depressed or hypersensitive cellular or humoral immune response system of a warm blooded animal, and/or reducing the adverse effects of stress on the above defense mechanisms of a warm blooded animal. This is accomplished by administering one or a mixture of ethereally monosubstituted monosaccharides having the general formula $M_1$—O—Y, and/or ethereal monosubstitutions of monosaccharide derivatives having the formula $M_2$—O—Y, and/or pharmaceutically acceptable organic acid and inorganic acid salts thereof as defined hereinafter. The above substances are administered to the warm blooded animal in effective amounts which are likewise defined hereinafter with greater particularity.

It is an object of the present invention to provide a novel method of enhancing the activity of phagocytes including macrophages in warm blooded animals.

It is a further object to provide a novel method of modulating the cellular or humoral immune response system of a warm blooded animal.

It is a further object to provide a novel method of enhancing the cellular or humoral immune response when a warm blooded animal has a normal to depressed cellular or humoral immune response system.

It is still a further object to provide a novel method of reducing the cellular or humoral immune response when a warm blooded animal has a hpersensitive cellular or humoral immune response system.

It is still a further object to provide a novel method of reducing the adverse effects of stress on the foregoing defense mechanisms of warm blooded animals.

Still other objects and advantages of the invention will be apparent to those skilled in this art upon reference to the following detailed description and the specific examples.

THE DETAILED DESCRIPTION OF THE INVENTION INCLUDING THE PRESENTLY PREFERRED VARIANTS THEREOF

In practicing one variant of the invention, a method is provided for enhancing the activity of phagocytes in warm blooded animals by administering a substance which comprises an ethereally monosubstituted monosaccharide having the general formula $M_1$—O—Y, and/or an ethereal monosubstitution of a monosaccharide derivative having the general formula $M_2$—O—Y, and/or a pharmaceutically acceptable organic acid and inorganic acid salt thereof as defined hereinafter. It is understood that the substances to be administered may include one or more of the above compounds. The phagocytes include macrophages in a normal to depressed or basal state of activation initially and macrophages already activated in response to infection, and the substance is administered in an amount effective to enhance the microbicidal activity of the phagocytes including the macrophages. In a second variant of the invention a method is provided for modulating the cellular or humoral immune response system of a warm blooded animal. In practicing this second variant, the above mentioned substance is administered to the warm blooded animal in an amount to enhance the cellular or humoral immune response when the warm blooded animal has a normal to depressed or basal cellular or humoral immune response system, or in an amount effective to reduce the cellular or humoral immune response when the warm blooded animal has a hypersensitive cellular immune response system. In still another variant of the invention, the aforementioned substance is administered to a warm blooded animal subject to stress in an amount effective to reduce the adverse effects of stress on the defense mechanisms and/or the resistance to disease. It is understood that there are certain preferred variants which produce unusual and unexpected results, and such preferred variants and/or the unusual and unexpected results produced thereby will be discussed in greater detail and with greater particularity hereinafter.

In the foregoing general formulae, $M_1$ is the residue of a nonderivatized monosaccharide selected from the group consisting of pentoses, hexoses and heptoses, and $M_2$ is the residue of a monosaccharide selected from the group consisting of pentoses, hexoses and heptoses which has been derivatized with (a) one or more alcohols containing 1–18 carbon atoms and preferably 1–4 carbon atoms to produce an ether group at one or more available hydroxyl groups or residua, (b) one or more aldehydes containing 1–18 carbon atoms and preferably 1–4 carbon atoms to produce single or multiple acetal groups at one or more available hydroxyl groups or residua, (c) one or more ketones containing 1–18 carbon atoms and preferably 1–4 carbon atoms to produce single or multiple ketal groups at one or more available hydroxyl groups or residua, or (d) one or more organic acid residua containing 1–18 carbon atoms and preferably 1–4 carbon atoms to produce ester groups at one or more available hydroxyl groups or residua. The above alcohols, aldehydes, ketones and acids may be either open or closed chain compounds, saturated or unsaturated, and substituted or unsubstituted. In each instance, Y is selected from the group consisting of cyclic monovalent nitrogen-containing organic radicals and residua free of oxygen attached only to a ring carbon atom and derived from a substance other than a monosaccharide, and monovalent organic radicals and residua having the general formula

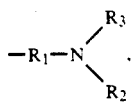

wherein $R_1$ is a divalent organic radical having a carbon chain length of about 1-7 carbon atoms and $R_2$ and $R_3$ are selected from the group consisting of —H, —OH, —SH, halogen and monovalent organic radicals and residua having a carbon chain length of about 1-7 carbon atoms. When $R_2$ or $R_3$ is halogen, the halogen may be F, Cl, Br or I, of which Cl and Br is usually preferred. The organic radical $R_1$, and $R_2$ and $R_3$ when they are organic radicals, may be branched or unbranched carbon chains and may be saturated or unsaturated, and when saturated, the unbranched and/or branched carbon chains may contain one or more double or triple carbon-to-carbon bonds. The unbranched and/or branched carbon chains of $R_1$, $R_2$ and $R_3$ may be substituted or unsubstituted, and when substituted, one or more substituents may be present, such as —OH, —SH, halogen (F, Cl, Br and/or I), branched or unbranched and saturated or unsaturated hydrocarbon radicals containing 1-7 and preferably 1-3 carbon atoms, —$OR_4$ and/or —$SR_4$ radicals, wherein $R_4$ is a branched or unbranched and saturated or unsaturated hydrocarbon radical containing 1-7 and preferably 1-3 carbon atoms, carboxylic acid residua containing 1-7 and preferably 1-3 carbon atoms, and amino groups and aminohydrocarbon radicals containing 1-7 and preferably 1-3 carbon atoms. Preferably $R_1$ is a hydrocarbon radical having a carbon chain length of 1-3 or 1-4 carbon atoms and $R_2$ and $R_3$ are individually selected from the group consisting of hydrogen and/or hydrocarbon radicals having carbon chain lengths of 1-3 or 1-4 carbon atoms.

Examples of compounds from which cyclic organic radicals and residua are derived include (a) monovalent nitrogen containing saturated, unsaturated or aromatic carbocyclic compounds containing about 4-8 carbon atoms in the ring and preferably about 5-6 carbon atoms in the ring and at least one nitrogen atom attached thereto or to an organo substituent thereon, (b) heterocyclic organic compounds containing about 3-8 carbon atoms in the ring and at least one ring nitrogen atom and (c) derivatives of the foregoing compounds wherein at least one substituent is present, such as —OH, —SH, halogen (F, Cl, Br and/or I), branched or unbranched and saturated or unsaturated hydrocarbon radicals containing 1-7 and preferably 1-3 carbon atoms, —$OR_5$ and/or —$SR_5$ radicals wherein $R_5$ is a branched or unbranched and saturated or unsaturated hydrocarbon radical containing 1-7 and preferably 1-3 carbon atoms, carbocyclic acid residua containing 1-7 and preferably 1-3 carbon atoms, and amino groups and aminohydrocarbon radicals containing 1-7 and preferably 1-3 carbon atoms. The aforementioned cyclic organic radicals and residua should be free of oxygen attached only to a ring carbon atom and also should be derived from a substance other than a monosaccharide.

The nonderivatized monosaccharide residue $M_1$ may exist in an open chain or cyclic form illustrated by the following general formulae:

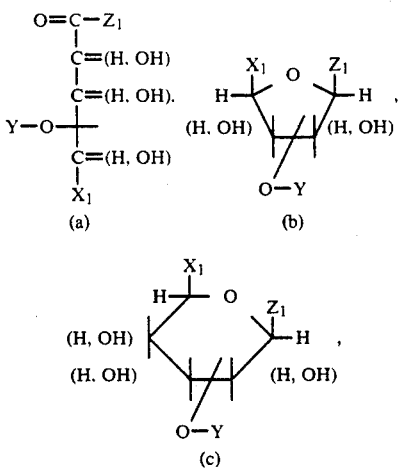

wherein $X_1$ and $Z_1$ are H, OH and/or hydroxyalkyl groups containing up to 3 carbon atoms, Y represents the same organic radicals and residua as aforementioned, and one of the OH groups, $X_1$ or $Z_1$ in each formula is replaced by —O—Y. The above general formulae (b) and (c) illustrate the pentacyclic and hexacyclic forms of the various isomers of the pentos hexoses and heptoses, the relative spatial configuration of the —H, and —OH groups about the rings, and the monosubstitution thereof in accordance with one presently preferred variant of the invention. The hydroxyl group of the hemiacetal or hemiketal linkage may assume an $\alpha$ or a $\beta$ configuration and the compounds may be in the form of anomers or mixtures of anomers.

The derivatized monosaccharide residue $M_2$ may exist in an open chain or cyclic form illustrated by the following general formulae:

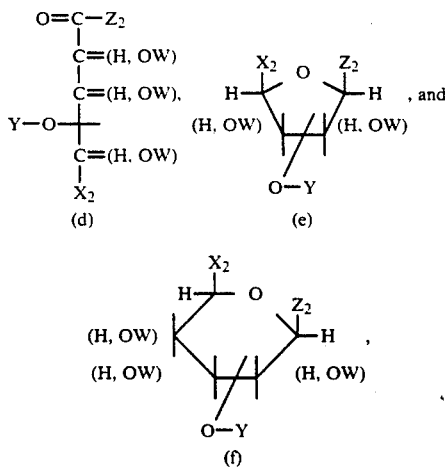

wherein $X_2$ and $Z_2$ are H, —OH, hydroxyalkyl, alkoxyl and/or alkoxyalkyl groups containing up to 3 carbon atoms, W is H, alkyl, alkenyl, cyclic alkane or cyclic aromatic groups containing 1-18 and preferably 1-6 carbon atoms or acyl groups containing 1-18 and preferably 1-4 carbon atoms, Y represents the same organic radicals and residua as aforementioned, and one of the OW groups $X_2$ or $Z_2$ in each formula is replaced by —O—Y. The above general formulae illustrate the various isomers of the pentoses, hexoses and heptoses, the relative spatial configuration of the —H and —OH groups about the ring and the derivatization thereof in accordance with one presently preferred variant of the invention. The hydroxyl or alkoxyl residue of the hemiacetal or hemiketal linkage may assume an α or a β configuration, and the derivatized monosaccharides may be in the form of anomers or mixtures of anomers.

The configuration of the various isomers and derivatives of the pentoses, hexoses and heptoses are well known to those skilled in this art and numerous reference books are available on the subject, the teachings of which are incorporated herein by reference, for example *Textbook of Biochemistry*, 4th Edition. by West et al (1966) and *The Monosaccharides* by Stanek, Cerny, Kocourek and Pacak (1963). The prior art discloses, for example, a total of eight open chain isomers for the reducing hexoses, and an even larger number of open chain isomers for the reducing heptoses. Either the dextrorotatory or D-series or the levorotatory or L-series of the pentoses, hexoses and heptoses may be used in practicing the invention, but it is usually preferred to use the D-series. The hexoses often give the best results and especially D-talose, D-galactose, L-galactose, D-idose, D-gulose, D-mannose, D-glucose, L-glucose, D-altrose and D-allose. The aforementioned pentoses, hexoses and heptoses may be derivatized at one or more of the hydroxyl groups, and is then ethereally substituted at one remaining available reactive position or positions. The ethereal substitution of certain available reactive positions of specific monosaccharide derivatives results in more therapeutically active or less toxic compounds. For instance, substitution of the 1-O- and 3-O-positions of glucose and the 6-O- position of galactose results in especially valuable compounds. Additionally, the ethereal substitution of the 3-O- position of 1,2-O-isopropylidene-D-glucofuranose or 1,2:5,6-di-O-isopropylidene-D-glucofuranose and the 6-O- position of 1,2-O-isopropylidene-D-galactopyranose or 1,2:3,4-di-O-isopropylidene-D-galactopyranose results in especially valuable compounds.

The following substituents, i.e., Y in the aforementioned general formulae $M_1$—O—Y or $M_2$—O—Y, may be ethereally substituted on any of the available reactive positions of the various isomers of the pentoses, hexoses and heptoses of $M_1$ or $M_2$ to produce nontoxic compounds having exceptional activity for the purposes of the present invention:
-(n-propylamino),
-(N',N'-dimethylamino-n-propyl),
-(N',N'-dimethylaminoisopropyl),
-(N'-methylpiperidyl),
-(N',N'-dimethylaminoethyl),
-(N',N'-diethylaminoethyl),
-(2',N',N'-trimethylamino-n-propyl),
-dimethylamino,
-(N',N'-dimethylaminomethyl),
-(N',N'-dimethylaminopropyl),
-(N',N'-dimethylamino-iso-butyl),
-(N',N'-dimethylamino-n-butyl),
-(N',N'-dimethylamino-iso-pentyl),
-(N',N'-dimethylaminopentyl),
-(N'-methylamino-n-propyl),
-(N'-methyl-N'-ethylamino-n-propyl),
-(N',N'-diethylamino-n-propyl),
-(amino-iso-propyl),
-(N'-ethylamino-n-propyl),
-(N'-propylamino-n-propyl),
-(N',N'-iso-propylamino-n-propyl),
-(1',2'-ethylamino-n-propyl),
-(1'-n-propylpyrrolidyl),
-(1'-n-propylpiperidyl),
-piperidyl, and
-(N',N'-dimethylamino-sec-butyl).

Of the foregoing, -(N', N'-dimethylamino-n-propyl) is presently preferred as Y in the formulae $M_1$—O—Y and $M_2$—O—Y and especially when substituted in the 1-O- and or 3-O-position of glucose or in the 6-O-position of galactose, or when substituted in the 3-O-position of 1,2-O-isopropylidene-D-glucofuranose or 1,2:5,6-di-O-isopropylidene-D-glucofuranose or the 6-O-position of 1,2-O-isopropylidene-D-galactopyranose or 1,2:3, 4-di-O-isopropylidene-D-galactopyranose.

The following compounds of the general formula $M_1$—O—Y have been found to have exceptional activity for use in the present invention:
3-O-3'-(n-propylamino)-glucose,
3-O-3'-(N', N'-dimethylamino-n-propyl)-gluocose,
3-O-4'-(N-methyl piperidyl)-glucose,
3-O-2'-(N', N'-dimethylaminoethyl)-glucose,
3-O-2'-(N', N'-diethylaminoethyl)-glucose,
3-O-3'-(2', N', N'-trimethylamino-n-propyl)-glucose,
α-N', N'-dimethylaminoisopropyl-glucoside,
6-O-3'-(N', N'-dimethylamino-n-propyl)-galactose,
3-O-2'-(N', N'-dimethylaminopropyl)-glucose
6-O-2'-(N', N',-dimethylaminopropyl)-galactose, and
pharmaceutically acceptable organic acid and inorganic acid salts thereof. The D-series of these compounds are preferred. Species of the foregoing compounds which are presently preferred are as follows:
3-O-3'-(N',   N'-dimethylamino-n-propyl)-D-glucopyranose,
3-O-4'-(N-methyl piperidyl)-D-glucopyranose,
3-O-2'-(N', N'-dimethylaminoethyl)-D-glucopyranose,
3-O-3'-(2',   N',   N'-trimethylamino-n-propyl)-D-glucopyranose,
α-N', N'-dimethylaminoisopropyl-D-glucoside,
6-O-3'-(N',   N'-dimethylamino-n-propyl)-D-galactopyranose,
3-O-2'(N',   N'-dimethylaminopropyl)-D-galactopyranose,
6-O-2'-(N',   N'-dimethylaminopropyl)-D-galactopyranose, and
pharmaceutically acceptable organic acid and inorganic acid salts thereof.

Additional compounds of the general formula $M_1$—O—Y, wherein Y is

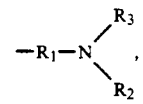

which may be used in practicing the invention are listed below:

| Monosaccharide Residue | Substituent (Y) | | |
| --- | --- | --- | --- |
| $M_1$ | $R_1$ | $R_2$ | $R_3$ |
| 3-O-D-glucofuranose | 3'-n-propyl | H | methyl |
| " | " | ethyl | " |
| " | " | H | ethyl |
| " | 2'-iso-propyl | methyl | methyl |
| " | 3'-1,2-propenyl | " | " |
| " | sec-butyl | " | " |
| " | 3'-butyl | " | " |
| " | 2'-ethyl | H . | H |
| " | methyl | H | H |

-continued

| Monosaccharide Residue $M_1$ | Substituent (Y) | | |
|---|---|---|---|
| | $R_1$ | $R_2$ | $R_3$ |
| 6-O-D-galactopyranose | 3'-n-propyl | H | methyl |
| " | " | ethyl | " |
| " | " | H | ethyl |
| " | 3'-1,2-propenyl | methyl | methyl |
| " | 2'-iso-propyl | " | " |
| " | sec-butyl | " | " |
| " | 3'-butyl | " | " |
| " | 2'-ethyl | H | H |
| " | methyl | H | H |

Still other compounds of the general formula $M_1$—O—Y, wherein Y is a cyclic monovalent nitrogen-containing organic radical or residue, which may be used in the method of the invention are as follows:

| Monosaccharide Residue $M_1$ | Substituent (Y) | |
|---|---|---|
| | Cyclic Radical | Substituent on the Cyclic Radical |
| 3-O-D-glucofuranose | 4'-piperidyl | H |
| " | 3'-piperidyl | methyl, H |
| " | 2'-piperidyl | " |
| " | 3'-pyrrolidyl | " |
| " | 2'-pyrrolidyl | " |
| 6-O-D-galactopyranose | 4'-piperidyl | H |
| " | 3'-piperidyl | methyl, H |
| " | 2'-piperidyl | " |
| " | 3'-pyrrolidyl | " |
| " | 2'-pyrrolidyl | " |

The following compounds of the general formula $M_2$—O—Y have exceptional wide spectrum activity and other valuable properties:

3-O-3'-(n-propylamino)-1,2-O-isopropylidene-D-glucofuranose,
3-O-3'-(N',N'-dimethylamino-n-propyl)-1,2-O-isopropylidene-D-glucofuranose,
3-O-4'-(N'-methylpiperidyl)-1,2-O-isopropylidene-D-glucofuranose,
3-O-2'-(N',N'-dimethylaminoethyl)-1,2-O-isopropylidene-D-glucofuranose,
3-O-2'-(N',N'-diethylaminoethyl)-1,2-O-isopropylidene-D-glucofuranose,
3-O-3'-(2',N',N'-trimethylamino-n-propyl)-1,2-O-isopropylidene-D-glucofuranose,
3-O-2'-(N',N'-dimethylaminopropyl)-1,2:5,6-di-O-isopropylidene-D-glucofuranose,
3-O-2'-(N',N'-dimethylaminopropyl)-1,2-O-isopropylidene-D-glucofuranose,
6-O-3'-(N',N'-dimethylamino-n-propyl)-1,2-O-isopropylidene-D-galactopyranose,
6-O-2'-(N',N'-dimethylaminopropyl)-1,2-O-isopropylidene-D-galactopyranose,
3-O-3'-(n-propylamino)-1,2:5,6-di-O-isopropylidene-D-glucofuranose,
3-O-3'-(N',N'-dimethylamino-n-propyl)-1,2:5,6-di-O-isopropylidene-D-glucofuranose,
3-O-4'-(N'-methylpiperidyl)-1,2:5,6-di-O-isopropylidene-D-glucofuranose,
3-O-2'-(N',N'-dimethylaminoethyl)-1,2:5,6-di-O-isopropylidene-D-glucofuranose,
3-O-2'-(N',N'-diethylaminoethyl)-1,2:5,6-di-O-isopropylidene-D-glucofuranose,
3-O-3'-(2',N',N'-trimethylamino-n-propyl)-1,2:5,6-di-O-isopropylidene-D-glucofuranose,
6-O-3'-(N',N'-dimethylamino-n-propyl)-1,2:3,4-di-O-isopropylidene-D-galactopyranose,
6-O-2'-(N',N'-dimethylaminopropyl)-1,2:3,4-di-O-isopropylidene-D-galactopyranose,
α-N',N'-dimethylamino-iso-propyl-2,3:5,6-di-O-isopropylidene-D-glucofuranoside, and organic and inorganic acid salts thereof.

Additional compounds of the general formula $M_2$—O—Y, wherein Y is

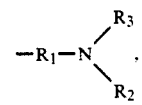

which may be used in the method of the invention are listed below:

| Monosaccharide Residue $M_1$ | Substituent (Y) | | |
|---|---|---|---|
| | $R_1$ | $R_2$ | $R_3$ |
| 3-O-1,2-O-isopropylidene-D-glucofuranose | 3'-n-propyl | H | methyl |
| 3-O-1,2-O-isopropylidene-D-glucofuranose | " | ethyl | " |
| 3-O-1,2-O-isopropylidene-D-glucofuranose | " | H | ethyl |
| 3-O-1,2-O-isopropylidene-D-glucofuranose | 2'-iso-propyl | methyl | methyl |
| 3-O-1,2-O-isopropylidene-D-glucofuranose | 3'-1,2-propenyl | " | " |
| 3-O-1,2-O-isopropylidene-D-glucofuranose | sec-butyl | " | " |
| 3-O-1,2-O-isopropylidene-D-glucofuranose | 3'-butyl | " | " |
| 3-O-1,2-O-isopropylidene-D-glucofuranose | 2'-ethyl | H | H |
| 3-O-1,2-O-isopropylidene-D-glucofuranose | methyl | H | H |
| 6-O-1,2-O-isopropylidene-D-galactopyranose | 3'-n-propyl | H | methyl |
| 6-O-1,2-O-isopropylidene-D-galactopyranose | " | ethyl | " |
| 6-O-1,2-O-isopropylidene-D-galactopyranose | " | H | ethyl |
| 6-O-1,2-O-isopropylidene-D-galactopyranose | 3'-1,2-propenyl | methyl | methyl |
| 6-O-1,2-O-isopropylidene-D-galactopyranose | 2'-iso-propyl | " | " |
| 6-O-1,2-O-isopropylidene-D-galactopyranose | sec-butyl | " | " |
| 6-O-1,2-O-isopropylidene-D-galactopyranose | 3'-butyl | " | " |
| 6-O-1,2-O-isopropylidene-D-galactopyranose | 2'-ethyl | H | H |
| 6-O-1,2-O-isopropylidene-D-galactopyranose | methyl | H | H |
| 3-O-1,2:5,6-di-O-isopropylidene-D-glucofuranose | 3'-n-propyl | H | methyl |
| 3-O-1,2:5,6-di-O-isopropylidene-D-glucofuranose | " | ethyl | " |
| 3-O-1,2:5,6-di-O-isopropylidene-D-glucofuranose | " | H | ethyl |
| 3-O-1,2:5,6-di-O-isopropylidene-D-glucofuranose | 2'-iso-propyl | methyl | methyl |
| 3-O-1,2:5,6-di-O-isopropylidene-D-glucofuranose | 3'-1,2-propenyl | " | " |
| 3-O-1,2:5,6-di-O-isopropylidene-D-glucofuranose | sec-butyl | " | " |
| 3-O-1,2:5,6-di-O-isopropylidene-D-glucofuranose | 3'-butyl | " | " |
| 3-O-1,2:5,6-di-O-iso- | 2'-ethyl | H | H |

-continued

| Monosaccharide Residue M₁ | Substituent (Y) | | |
|---|---|---|---|
| | R₁ | R₂ | R₃ |
| propylidene-D-glucofuranose | | | |
| 3-O-1,2:5,6-di-O-isopropylidene-D-glucofuranose | methyl | H | H |
| 6-O-1,2:3,4-di-O-isopropylidene-D-galactopyranose | 3'-n-propyl | H | methyl |
| 6-O-1,2:3,4-di-O-isopropylidene-D-galactopyranose | " | ethyl | " |
| 6-O-1,2:3,4-di-O-isopropylidene-D-galactopyranose | " | H | ethyl |
| 6-O-1,2:3,4-di-O-isopropylidene-D-galactopyranose | 3'-1,2-propenyl | methyl | methyl |
| 6-O-1,2:3,4-di-O-isopropylidene-D-galactopyranose | 2'-iso-propyl | " | " |
| 6-O-1,2:3,4-di-O-isopropylidene-D-galactopyranose | sec-butyl | " | " |
| 6-O-1,2:3,4-di-O-isopropylidene-D-galactopyranose | 3'-butyl | " | " |
| 6-O-1,2:3,4-di-O-isopropylidene-D-galactopyranose | 2'-ethyl | H | H |
| 6-O-1,2:3,4-di-O-isopropylidene-D-galactopyranose | methyl | H | H |

Still other compounds of the general formula $M_2$—O—Y wherein Y is a cyclic monovalent nitrogen-containing organic radical or residue, which may be used in the method of the invention are as follows:

| Monosaccharide Residue M₂ | Substituent (Y) | |
|---|---|---|
| | Cyclic Radical | Substituent on the Cyclic Radical |
| 3-O-1,2-O-isopropylidene-D-glucofuranose | 4'-piperidyl | H |
| 3-O-1,2-O-isopropylidene-D-glucofuranose | 3'-piperidyl | methyl, H |
| 3-O-1,2-O-isopropylidene-D-glucofuranose | 2'-piperidyl | " |
| 3-O-1,2-O-isopropylidene-D-glucofuranose | 3'-pyrrolidyl | " |
| 3-O-1,2-O-isopropylidene-D-glucofuranose | 2'-pyrrolidyl | " |
| 6-O-1,2-O-isopropylidene-D-galactopyranose | 4'-piperidyl | H |
| 6-O-1,2-O-isopropylidene-D-galactopyranose | 3'-piperidyl | methyl, H |
| 6-O-1,2-O-isopropylidene-D-galactopyranose | 2'-piperidyl | " |
| 6-O-1,2-O-isopropylidene-D-galactopyranose | 3'-pyrrolidyl | " |
| 6-O-1,2-O-isopropylidene-D-galactopyranose | 2'-pyrrolidyl | " |
| 3-O-1,2:5,6-di-O-isopropylidene-D-glucofuranose | 4'-piperidyl | H |
| 3-O-1,2:5,6-di-O-isopropylidene-D-glucofuranose | 3'-piperidyl | methyl, H |
| 3-O-1,2:5,6-di-O-isopropylidene-D-glucofuranose | 2'-piperidyl | " |
| 3-O-1,2:5,6-di-O-isopropylidene-D-glucofuranose | 3'-pyrrolidyl | " |
| 3-O-1,2:5,6-di-O-isopropylidene-D-glucofuranose | 2'-pyrrolidyl | " |
| 6-O-1,2:3,4-di-O-isopropylidene-D-galactopyranose | 4'-piperidyl | H |
| 6-O-1,2:3,4-di-O-isopropylidene-D-galactopyranose | 3'-piperidyl | methyl, H |
| 6-O-1,2:3,4-di-O-isopropylidene-D-galactopyranose | 2'-piperidyl | " |
| 6-O-1,2:3,4-di-O-isopropylidene-D-galactopyranose | 3'-pyrrolidyl | " |
| 6-O-1,2:3,4-di-O-isopropylidene-D-galactopyranose | 2'-pyrrolidyl | " |

In general, the preparation of compounds of the formula $M_1$—O—Y described herein involves the formation of cyclic organo amine ethers or alkyl amine ethers of substituted cyclic organo amine ethers or alkyl amine ethers at selected positions on the desired nonderivatized monosaccharide, such as at position 1-O-or 3-O- of D-glucose, position 6-O- of D-galactose, and position 3-O- of D-fructose. Similarly, the preparation of compounds of the formula $M_2$—O—Y described herein involves the formation of the aforementioned types of ethers at selected positions on the desired monosaccharide derivative, such as at position 3-O- of 1,2-O-isopropylidene-D-glucofuranose or 1,2:5,6-di-O-isopropylidene-D-glucofuranose, position 6-O- of 1, 2-O-isopropylidene-D-galactopyranose or 1,2:3,4-di-O-isopropylidene-D-galactopyranose, and position 3-O- of 1,2-O-isopropylidene-D-fructopyranose or 1,2:5,6-di-O-isopropylidene-D-fructopyranose. The condensation of the substituent substrate with the desired nonderivatized monosaccharide or the monosaccharide derivative at the desired position may be achieved by various prior art techniques. One method is described in U.S. Pat. No. 2,715,121, issued Aug. 9, 1955, to Glen, et al, the disclosure of which is incorporated herein by reference. The method described in this patent requires extreme reaction conditions and often gives low yields. The product purity is also less than satisfactory.

The preferred method of preparation is described in my U.S. Pat. No. 4,056,322, the disclosure of which is incorporated herein by reference, and involves much milder reaction conditions than employed in U.S. Pat. No. 2,715,121. The side reactions are minimized, the purity of the final product is greatly improved and the method may be adapted to a series of solvents having varying properties such as dioxane, tetrahydrofuran and benzene. The improved method involves the reaction of a monoaccharide derivative which is blocked with one or more organo groups in the hydroxl group positions adjacent the desired position to be substituted. The blocked monosaccharide is dissolved in one of the foregoing solvents and is reacted with a halogenated organo amino compound having the desired carbon chain length and configuration in the presence of a base such as sodium hydroxide. The resulting products are compounds of the formula $M_2$—O—Y, which are blocked derivatives of the compounds $M_1$—O—Y of the invention. Selective removal of one or more blocking groups may be accomplished by hydrolysis under specific conditions resulting in a new product which is to be considered a compound suitable for use in this invention. The reaction of either the blocked compound or the hydrolyzed compound with organic or inorganic acids to form a salt thereof also results in a compound suitable for use in this invention.

It is understood that simple derivatives of the compounds described herein may be used in practicing the invention. Such derivatives may be prepared by prior art techniques and procedures. For example, the free amine compounds are basic and form organic acid salts and inorganic acid salts, and the resulting salts are useful in the method of the invention. The salts may be prepared by the usual prior art techniques, such as by adding the free amine compound to water and then adding the desired organic acid or mineral acid thereto in an amount sufficient to neutralize the free amine. Examples of suitable acids include HCl, HBr, $H_2SO_4$, $HNO_3$, benzoic acid, p-aminobenzoic acid, p-acetamidobenzoic acid p-hydroxybenzoic acid, alkane sulfonic acids, p-toluene sulfonic acid, acetic acid, alkylcarboxylic acids, oxalic acid, tartaric acid, lactic acid, pyruvic acid, malic acid, succinic acid, gluconic acid and glucuronic acid. The aqueous solution of the resulting salt is evaporated to the volume necessary to assure precipitation of the salt upon cooling. The precipitated salt is recovered by filtration washed and dried to obtain a final amine salt product. The amine salts are often preferred for use in formulating the therapeutic compositions of the invention as they are crystalline and relatively nonhygroscopic. The amine salts are also better adapted for intramuscular injection than are the free amines.

Prior art blocking or derivatizing techniques may be employed such as acetonization and acetylation. Suitable prior art blocking or derivatizing methods are described in the aforementioned U.S. Pat. No. 2,715,121 and 4,056,322. The alcohols used to produce an acetal group may contain 1-18 and preferably 1-4 carbon atoms. Specific examples include methyl, ethyl, propyl, isopropyl, butyl, isobutyl, amyl, and isoamyl alcohols. In instances where an aldehyde or ketone is reacted with hydroxyl groups on adjacent carbon atoms, the initial compound may be dissolved in the desired aldehyde or ketone under anhydrous conditions and a Lewis acid catalyst is added in a catalytic quantity, such as 1% zinc chloride or anhydrous phosphoric acid. Often acetone is the preferred blocking or derivatizing agent, but aldehydes or ketones of much higher molecular weight may be used when desired such as those containing up to 18 carbon atoms and preferably 1-8 or about 2-4 carbon atoms. Specific examples of additional ketones include methyl ethyl ketone, diethyl ketone, ethyl propyl ketone and dipropyl ketone. Specific examples of aldehydes include acetaldehyde, propionaldehyde, and butyraldehyde. The reaction mixture is agitated at room temperature for a prolonged reaction period, such as 24-48 hours. The compound may be blocked or derivatized in a plurality of positions, such as the 1,2- and 5,6-positions. It is usually preferred to block or derivatize positions such as the 1,2-positions as the resulting partially blocked or derivatized compound is much less toxic than compounds blocked or derivatized in all available hydroxyl groups.

It is also possible to block or derivatize one or more free hydroxyl positions of the compound with an ester group, wherein the carboxylic acid residue contains 1-18 and preferably about 1-3 carbon atoms. Specific examples of organic acids include formic acid, acetic acid, propionic acid and butyric acid. The ester derivatives likewise may be prepared following prior art techniques such as by reacting a carboxylic acid anhydride with the compound following prior art practices. Additionally, the $\alpha$ or $\beta$ alkyl derivatives of nonderivatized monosaccharides or of monosaccharide derivatives such as 2,3:5,6-di-O-isopropylidene-D-glucofuranoside may be prepared following prior art techniques. In this latter instance, the compound is dissolved in a dry alcohol having the desired carbon chain length with the aforementioned residua and reacted with the compound in the presence of a catalyst such as the hydrogen chloride of Dowex 5-H+ resin. While the above discussed derivatives are presently preferred, it is understood that still other simple derivatives may be prepared following prior art techniques and then used in practicing the present invention.

The groups used in derivatizing $M_2$ of the formula $M_2$—O—Y are preferably labil organo groups, such as acetal or ketal groups, which are easily hydrolyzable or otherwise easily removed from the residue of the monosaccharide. For best results, the derivatizing groups should be easily removed in situ following administering the compound $M_2$—O—Y to a warm blooded animal to thereby produce the active compound $M_1$—O—Y.

The compounds used in the method of the present invention may be administered to human patients or lower warm blooded animals to be treated either orally or by parenteral administration, and either with or without a pharmaceutically acceptable carrier. When the compound is to be administered orally, it may be admixed with a prior art filler and/or binder such as starch and a disintegrator, and the admixture may be pressed into a tablet of a size convenient for oral administration. Capsules also may be filled with a composition containing the compound, with or without a filler, and administered orally. Alternatively, a water solution or suspension of the compound, or an admixture thereof with a flavored syrup such as cherry syrup, may be administered orally. When the compound is administered by intramuscular injection, it is usually dissolved in a physiological saline solution which contains sodium chloride in sufficient concentration to make the overall solution to be injected isotonic to body fluids. A salt of the free amine is usually preferred in instances where the compound is administered by intramuscular injection. In treating some patients or when convenient, the salt form of the compound in aqueous solution may also be administered by nasopharyngeal spray. Administration also may be by means of a suppository in patients unable to retain medication administered by mouth. Suitable pharmaceutically acceptable carriers and techniques in addition to those mentioned above may be used when desired.

The dosage may be varied over extremely wide limits, as the compounds are effective at low dosage levels and are nontoxic and free of adverse side effects. The compounds may be administered in the minimum quantity which is effective, and the dosage may be increased as desired up to the maximum effective dosage tolerated by the patient. Animal toxicity data indicate that the limiting nontoxic dosage may be 100-1000 or more times the minimum effective dosage. As a general rule, oral drug toxicity does not appear until the dosage exceeds 10 grams per kilogram of body weight per day and thus it is not necessary to carefully control the dosage for patients sensitive to the prior art drugs. The compound is usually administered in an amount of about 0.001-1000 milligrams, or for better results about 0.01-500 milligrams, per kilogram of body weight per day, and preferably in an amount of about 0.1-100 milligrams per kilogram of body weight per day, over the period required for treatment. In some instances better results are obtained at dosage levels of about 1-20 milligrams, and best results at about 10 milligrams, per kilogram of body weight per day.

The prophylactic method of the invention is especially useful in treating human patients, but lower warm blooded animals also may be treated. For example, domestic animals and pets such as horses, bovines in general, sheep, goats, swine, cattle, poultry, birds and fowls in general, dogs, cats and the like may be prophylactically treated in accordance with the invention. The foregoing are collectively referred to herein as being warm blooded animals.

The present invention is very useful in enhancing the microbicidal activity of phagocytes, including macrophages in a normal to depressed state of activation or macrophages already activated in response to infection, and in enhancing the cellular or humoral immune response in warm blooded animals having a normal to depressed cellular or humoral immune response system. This is especially true in instances where the activity of the phagocytes or the cellular or humoral immune response system is depressed by environmental conditions or for other reasons. For example, the depression may be due to stress, common air pollutants, drugs, and radiation used in treating cancer. The invention is useful in relieving or reducing the adverse effects of stress on warm blooded animals. In such instances, the warm blooded animals do not have a disease initially, but are very susceptible to infections and cannot be treated by prior art theraphy. Thus, the depressed state of activation of the phagocytes and/or the immune response system allow infections to sicken and sometimes overwhelm the warm blooded animal before adequate therapeutic treatment can be given.

The method of the invention is especially useful in enhancing the function of macrophages and T-lymphocyte cell systems, and in increasing their capacity to modulate immunity and to destroy invading organisms that are ingested thereby, including bacteria, such as salmonella, mycobacteria, listeria, shigella, E. coli, staphylococcus and others, fungi, as candida, actinomyces, coccidordes, blastomyces, histoplasma and others, viruses, including DNA and RNA viruses, both capsulated and uncapsulated, budding and lytic, as herpesvirus and related organisms, mumps virus, influenza, vaccinia, variola, rhinoviruses and others, plasmodia, as malaria and others, and trypanosomes and other protozoa. A similar enhancement of microbial killing is effected in the polymorphonuclear leukocytes or microphages.

The method of the invention increases the amount of hydrogen peroxide generated by macrophages and microphages and the amount of hydrogen peroxide-utilizing enzymes, catalase and peroxidase in these cells. The prior art has established that peroxide and the secreted enzymes are of prime importance to and may underlie the antimicrobial action of the macrophage and microphage phagocytes. The method of the invention also increases the amount of other intracellular enzymes that are associated with microbicidal activity. These enzymes include acid phosphatase, beta-galactosidase and others.

The method of the invention also increases the amount of protein synthesized in and secreted by macrophages, microphages and T-lymphocytes. This secretion also serves microbicidal ends as well. The antimicrobial protein interferon is produced by macrophages and lymphocytes and the quantity is increased in this secretion. Further, regulators of the immune response are secreted by macrophages and T-lymphocytes in greater amounts. Lysosomal hydrolytic enzymes, such as acid phosphatase and proteases which can enhance arthritic and other kinds of nonspecific tissue inflammation, are not enhanced in their secretion by treatment with compounds of the invention.

In association with an enhanced secretion of compounds that regulate immune responses, the method of the invention acts to enhance both down-regulating and up-regulating controls of the immune system. When the immune response is very high or hypersensitive, the net effect of the method is a down-regulation of the immune response. When the immune response is weak because of immunodepression influences, as stress, intoxication from metal pollutants or use of immunodepressive medical treatment, the effect of the method of the invention will be to up-regulate or increase the immune responses. This activity is an immunological buffering action and is an effective treatment for rheumatoid arthritis, lupus erythematosis, eczema and other diseases of autoimmunity in which down-regulating functions as exerted by depressor T-lymphocytes or depressor macrophages may be hypoactive.

The foregoing detailed description and the following specific examples are for purposes of illustration only, and are not intended as being limiting to the spirit or scope of the appended claims.

Examples I, II, XI, XII, XVI and XIX report work actually performed, Example XIV reports work actually performed with compound 1213; it is hypothetical with respect to compound 1211. Examples III-X, XIII, XV, XVII, and XVIII are hypothetical,

EXAMPLE I

Well-established methodology of the prior art was employed to determine the antimicrobial potency of 1,2-O-isopropylidene-3-O-3'-(N',N'-dimethylamino-n-propyl)-D-glucofuranose (SM-1213) against the bacterium Listeria monocytogenes in guinea pig paraffin oil-elicited macrophages and microphages at 37° C. (see Leu, R. W., Eddleston, A. L. W. F., Hadden, J. W., and Good, R. A., J. exp. Med. 136:589, 1972).

Macrophages were harvested from the peritoneal cavity of guinea pigs that had received an injection of paraffin oil 72 hours previously. Macrophages were washed three times with phosphate-buffered saline and allowed to form monolayers in Falcon flasks in the presence of HI-WO$_5$/BA$_{2000}$ culture medium (International Scientific Industries). Two hours later, monolayers comprising approximately $5 \times 10^6$ cells were exposed to $1 \times 10^6$ organisms of L. monocytogenes. Thirty minutes later, medium containing unphagocytosed cells was poured off and replaced with medium that contained either no drug or SM-1213 at either 0.1 µg/ml or 1.0 µg/ml.

At 30 minutes following media change and at 6 hours, Listeria-infected cultures were evaluated for Listeria content. One hundred cells chosen at random were evaluated for Listeria content at each time period and the increase in Listeria cell mass determined (Table I).

TABLE I

| Relative Increase in Bacterial Cell Mass Within Macrophages | |
|---|---|
| Control | 100% |
| SM-1213, 0.1 μg/ml | 0%[a] |
| SM-1213, 1.0 μg/ml | 30%[b] |

[a] $P < 0.001$.
[b] $P < 0.01$.

These results indicate that SM-1213 exerts a highly significant antibacterial effect within macrophages.

The above procedure may be carried out employing 3-O-3'-(N',N'-dimethylamino-n-propyl)-D-glucose (SM-1211) with essentially the same results.

EXAMPLE II

Well-established methodology of the prior art is employed to determine the antimicrobial potency of SM-1211 and SM-1213 against the fungus *Candida albicans* in guinea pig paraffin oil-elicited macrophages and microphages at 37° C. (see Leu, R. W., Eddleston, A. L. W. F., Hadden, J. W., and Good, R. A., *J. exp. Med.* 136:589, 1972).

Macrophages are harvested from the peritoneal cavity of guinea pigs that have received an injection of paraffin oil 72 hours previously. Macrophages are washed three times with phosphate-buffered saline and allowed to form monolayers in F Falcon flasks in the presence of HI-WO$_5$/BA2000 culture medium (International Scientific Industries). Two hours later, monolayers comprising approximately $5 \times 10^6$ cells are exposed to $1 \times 10^6$ organisms of *C. albicans*. Thirty minutes later, medium containing unphagocytosed cells is poured off and replaced with medium that contains either no drug, SM-1211 at 0.001, 0.1 or 1.0 μg/ml, or SM-1213 at 0.001, 0.1 or 1.0 μg/ml.

At five hours following media, the average length of hyphal growth of fungi within macrophages is assessed by a high-powered microscope. Forty fungi in each treatment group are assessed. The results indicate that SM-1211 and SM-1213 exert a highly significant antifungal effect within macrophages.

EXAMPLE III

Well-established methodology of the prior art is employed to determine the antimicrobial potency of SM-1211 and SM-1213 against the gram-negative bacterium *Listeria monocytogenes* in mice. Listeria ($4 \times 10^6$ organisms) is injected intraperitoneally into young adult Balb/c mice, who are then given drinking water containing 0.1 mg/ml of either SM-1211 or SM-1213. Mortality is determined in control and treated groups at day 5. The results indicate that SM-1211 and SM-1213 suppress the early mortality of mice infected with *L. monocytogenes*, and exemplify for this organism the broad spectrum increase in resistance to infection induced by the compounds of the invention.

EXAMPLE IV

Well-established methodology of the prior art is employed to determine the antimicrobial potency of SM-1211 and SM-1213 against the gram-negative bacterium *Salmonella flexneri* in mice. Salmonella ($5 \times 10^6$ organisms) is injected intraperitoneally into young adult Balb/c mice, who are then given drinking water containing 0.1 mg/ml of either SM-1211 or SM-1213. Mortality is determined in control and treated groups at day 5. The results indicate that SM-1211 and SM-1213 suppress the early mortality of mice infected with *S. flexneri*, and exemplify for this organism the broad spectrum increase in resistance to infection induced by compounds of the invention.

EXAMPLE V

Well-established methodology of the prior art is employed to determine the antimicrobial potency of SM-1211 and SM-1213 against the gram-positive bacterium *Streptococcus pneumoniae* in mice. One day before infection, animals are given drinking water containing 0.1 mg/ml of either SM-1211 or SM-1213. The next day, *S. pneumoniae* ($10^2$ organisms) is injected intraperitoneally into young adult Balb/c mice. Drug treatment is continued through day 2, when mortality is determined. The results indicate that SM-1211 and SM-1213 suppress the early mortality of mice infected with *S. pneumoniae*, and exemplify for this organism the broad spectrum increase in resistance to infection induced by the compounds of the invention.

EXAMPLE VI

Well-established methodology of the prior art is employed to determine the antimicrobial potency of SM-1211 and SM-1213 against the bacterium *Mycobacterium tuberculosis* in rabbits. New Zealand white rabbits are injected intradermally in multiple sites with the Phipps strain of Bacillus-Calmette-Guerin (BCG). Ten control rabbits and ten rabbits given 0.5 mg/kg of either SM-1211 or SM-1213 are employed. Intradermal lesions are biopsied serially and examined for macrophage activation by the histochemical assessment of levels of β-galactosidase activity. Biopsied specimens are stained with carbol fuchsin for acid-fast bacilli and counterstained with hematoxylin. β-galactosidase activity is scored as +1 (1% or less of macrophages demonstrating activity), +2 (2-3%), +3 (4-5%), or +4 (more than 5%). The rate of lesion healing is assessed at days 10, 14, 20, 30, 40 and 60. The results indicate that the rate of lesion healing is significantly accelerated by treatment with SM-1211 and SM-1213 in association with an enhancement of galactosidase activity in macrophages, and exemplify for this organism the broad spectrum increase in resistance to infection induced by the compounds of the invention.

EXAMPLE VII

Well-established methodology of the prior art is employed to determine the antimicrobial potency of SM-1211 and SM-1213 against the fungus *Candida albicans*. Female mice are injected intravenously with $4 \times 10^4$ viable units of *C. albicans*. Following infection, treated animals are given either SM-1211 or SM-1213 in the drinking water at concentrations of either 0.1 or 0.01 mg/ml. Animals ingest drug ad libitum, achieving average levels of between 1.5 and 15 mg/kg per 24 hours. At day 5 post-infection, the Candida content of liver, spleen and kidneys is determined by standard sensitivity plate techniques (Rogers, T., and Balish, E., *Infect. Immun.* 14:33, 1976). The results indicate that SM-1211 and SM-1213 exert a significant antifungal effect in mammals.

EXAMPLE VIII

Well-established methodology of the prior art is employed to determine the antimicrobial potency of SM-1211 and SM-1213 against the haemoflagellate *Trypanosoma cruzi* in mouse macrophages (Kress, Y., Bloom, B.

R., Wittner, M., Rowen, A., and Tanowitz, H., *Nature* 257:394, 1975).

Normal macrophages are collected from the peritoneal cavity of C57 black mice by lavage with ice-cold Hanks' solution containing 5 IU ml$^{-1}$ of heparin. These macrophages are cultured at $2 \times 10^6 - 3 \times 10^6$ cells per ml in 10% fetal bovine serum on coverslips in Leighton tubes, containing either no drug or SM-1211 or SM-1213 at concentrations of 0.01 or 0.1 μg/ml. Cultures are infected with *T. cruzi* as 7-d cultures, primarily epimastigote forms as 1:1 and 10:1 parasite-macrophage ratio. After 2 hours, coverslips are washed three times with agitation to remove free swimming forms, and replaced with fresh medium and observed at 2, 24, 48, 72, 96 and 192 hours after infection. Details for preparation of coverslips for electron microscopic examination are carried out according to the methodology of Jones and Hirsch (*J. exp. Med.* 136:1173, 1972). Survival of intact *T. cruzi* in macrophages is assessed by electron microscopic scanning of 100 consecutive macrophages from 24-hour and 96-hour cultures. The results indicate that treatment with SM-1211 and SM-1213 enhances the capacity of mouse macrophages to destroy ingested trypanosomes.

EXAMPLE IX

To confirm that the antiparasite action of SM-1211 and SM-1213 in macrophages shown above in tissue culture can protect the living animal, well-established methodology of the prior art is employed to determine the antimicrobial potency of SM-1211 and SM-1213 against the haemoflagellate *Trypanosoma cruzi* in mice (Williams, D. M., Sawyer, S., and Remington, J. S., *J. Infect. Dis.* 134:610, 1976).

Determinations are made of survival rates after intraperitoneal challenge with $5 \times 10^4$ *T. cruzi* of control mice and mice given as drinking water solutions containing 0.1 or 0.01 mg/ml of either SM-1211 or SM-1213. Drug solutions are provided ad libitum at 24 hours before infection. Death rates are assessed at 12, 14 and 20 days. The results indicate that SM-1211 and SM-1213 suppress the disease caused in mammals by *T. cruzi*. Since human forms of this condition are widespread in many parts of the globe, the significance of such chemotherapeutic effects speaks for itself.

EXAMPLE X

Well-established methodology of the prior art is employed to determine the antimicrobial potency of SM-1211 and SM-1213 against the mouse malaria organism *Plasmodium berghei* in mice. The NYU-2 strain of *P. berghei* is maintained by weekly intraperitoneal transfer in Balb/c mice. The blood from infected mice is obtained by transection of the axillary artery and vein. The erythrocytes are washed twice with 0.85% NaCl. A smear of the washed erythrocytes is stained with Giemsa, and the percentage of parasitized erythrocytes is determined. The inoculum is adjusted with saline to a concentration of $10^3$ parasitized erythrocytes/ml, and each mouse is given an intraperitoneal injection of 1 ml of the inoculum. At day −1 or at day 6, mice are given drinking water containing 0.1 mg/ml of either SM-1211 or SM-1213. Mortality is determined at day 12. The results indicate that SM-1211 and SM-1213 suppress the early mortality of mice infected with *P. berghei*, and exemplify for this organism the broad spectrum increase in resistance to infection induced by the compounds of the invention.

EXAMPLE XI

Well-established methodology of the prior art was employed to determine the effect of 3-O-2'-(N',N'-dimethylaminoisopropyl)-D-glucose on cell-mediated immune responses in the skin of guinea pigs (see Zinsser, H., *J. exp. Med.* 34:495, 1921). The cellular immune response, evaluated as delayed hypersensitivity was determined 8, 10 and 12 days after immunization of guinea pigs with killed tubercle bacilli (complete Freund's adjuvant, Difco, Detroit) diluted with 9 parts of incomplete adjuvant (paraffin oil). Skin challenge was effected on the days cited by the use of second strength purified protein derivative (Parke-Davis PPD).

In this study, 80 mg/kg of either 3-O-2'-(N',N'-dimethylamino-isopropyl)-D-glucose or 3-O-methyl glucose, or saline, was administered subcutaneously once daily from day 1 through day 13. Challenge was made with 12.5 μg of PPD in two sites per guinea pig. Readings were made 24 and 48 hours after challenge. Results are given for the day 12 challenge (Table II).

TABLE II

| | Cell-Mediated Immune Response | | | |
|---|---|---|---|---|
| | | Average Skin | Statistics | |
| | N | Response Radius at 24 hours | Saline Control | 3-O-Methyl Glucose |
| Saline control | 16 | 0.59 | | |
| 3-O-methyl glucose | 5 | 0.60 | | |
| 3-O-2'-(N',N'-dimethylamino-isopropyl)-D-glucose | 11 | 2.00 | $P < 0.001$ | $P < 0.01$ |

These data indicate that treatment with 3-O-2'-(N',N'-dimethylamino-isopropyl)-D-glucose increases the cellular immune response of guinea pigs by 240%, a very significant change.

The above procedure may be carried out employing SM-1213 with essentially the same results.

EXAMPLE XII

Well-established methodology of the prior art was employed to determine the enhancement of the depressed cellular immune response system by SM-1213. In contrast to male mice, female mice do not fight with each other when housed 12 to a cage. When housed in relative isolation (2 mice to a cage, giving each mouse 150 cm$^2$ of floor space), female mice exhibit immunodepression (Glen, W. G., and Becker, R. E., *J. Physiol. Zool.* 42:411, 1969).

In this study, female mice with imposed social stress were housed 2 to a cage, whereas the groups without imposed social stress were housed 12 to a cage. Female mice of the Ha/ICR random-bred strain were immunized by the subcutaneous route with 0.2 ml of a 25% suspension containing $10^9$ washed human type O red blood cells. SM-1213 was added to the drinking water 6 days following immunization at a dose of 80 mg/kg/day. Drug therapy was continued throughout the rest of the experiment.

At 14 and 28 days following immunization, the animals were challenged with the same antigen ($10^8$ cells in 0.03 ml) inoculated subcutaneously in one hind paw. In some experiments, as an unrelated antigen control the other hind paw was inoculated with horse red blood cells. Swelling of the inoculated paws was evaluated by direct examination (coded animals being scored single-blind on a scale of 0-4+ swelling by two independent observers) or by measurement of one diameter with a micrometer. Paw swelling was evaluated at 24 and 48 hours following challenge (Table III).

TABLE III

| | 24/48 Hour Paw Swelling | |
|---|---|---|
| | 12 Mice/Cage (mm × $10^{-2}$) | 2 Mice/Cage (mm × $10^{-2}$) |
| Day 14 challenge | | |
| Control | 94 ± 16 | 38 ± 6 |
| Day 28 challenge | | |
| Control | | 58 ± 13 |
| SM-1213 | | 116 ± 16 |

These data indicate that, when cellular immune responses are depressed as by psychosocial stress, SM-1213 strikingly increases cellular immune responses. Depression of cellular immunity is associated with vulnerability to a large number of infections, as by herpesvirus, vaccinia virus, fungi and other microorganisms. The capacity of drugs to significantly enhance cellular immunity under conditions of its depression will be associated with the desired restoration of host antimicrobial defenses.

The above procedure may be carried out employing SM-1211 with essentially the same results.

EXAMPLE XIII

Well-established methodology of the prior art is employed to determine the enhancement of the depressed cellular immune response system by SM-1211 and SM-1213. The procedure described in Example XII is employed, except that immuno-depression is induced by housing the mice 2 to a cage and by the daily injection of 20 mg/kg cyclophosphamide. The results indicate that, when cellular immune responses are depressed as by psychosocial stress and compounds that suppress the function of leukocytes and are normally used in the treatment of leukemias, SM-1211 and SM-1213 strikingly increase cellular immune responses.

EXAMPLE XIV

Well-established methodology of the prior art is employed to determine the depression of the hypersensitive cellular and humoral immune response systems by SM-1211 and SM-1213. Immune responses are known to be modulated by the body's hormones. Particularly important for such actions are hormones of the hypothalmus-pituitary-adrenal cortex axis. Thus, adrenocortical hormones are known to depress immunity, while pituitary hormones of the growth hormone and thyrotropic hormone types are known to enhance immunity.

Ten days before immunization, cellular and humoral immune responses are elevated above normal levels by placing female mice of the Ha/ICR random-bred strain on a 3 times per week regimen of 1 IU growth hormone, injected subcutaneously. The mice are immunized by the subcutaneous route with 0.2 ml of a 25% suspension containing $10^9$ washed human type O red blood cells. SM-1211 or SM-1213 is added to the drinking water 6 days following immunization at a dose of 80 mg/kg/day. Drug therapy is continued throughout the rest of the experiment.

At 14 and 28 days following immunization, the animals are challenged with the same antigen ($10^8$ cells in 0.03 ml) inoculated subcutaneously in one hind paw. In some experiments, as an unrelated antigen control the other hind paw is inoculated with horse red blood cells. Swelling of the inoculated paws is evaluated by direct examination (coded animals being scored single-blind on a scale of 0-4+ swelling by two independent observers) or by measurement of one diameter with a micrometer. Paw swelling is evaluated at 24 and 48 hours following challenge to determine cellular immunity. Humoral immunity is determined by bleeding the animals at day 16 for hemagglutinin antibody titers to the immunizing red blood cells. The results indicate that exaggerated immune responses provoked by hormonal imbalance can be restored to normal levels by treatment with SM-1211 and SM-1213. The benefits of such a drug action will lie in the chemotherapy of autoimmune diseases, in which exaggerated immune responses to body components are the rule.

EXAMPLE XV

Well-established methodology of the prior art was employed to determine the enhancement of the depressed humoral immune response system by SM-1213. In this experiment, immunodepression was induced by viral infection.

Male mice of the A/J strain were immunized by the subcutaneous route with 0.2 ml of a 25% suspension containing $10^9$ washed human type O red blood cells. On day 5, mice were infected intraperitoneally with 300 PFU herpes simplex virus. SM-1213 was added to the drinking water 6 days following immunization at a dose of 80 mg/kg/day. At 10 days following immunization, the animals were challenged with the same antigen ($10^8$ cells in 0.03 ml) inoculated subcutaneously in one hind paw. Humoral immunity was determined by bleeding the animals at day 13 for hemagglutinin antibody titers to the immunizing red blood cells (Table IV).

TABLE IV

| Hemagglutinin Antibody Titers | |
|---|---|
| | $Log_2$ |
| Uninfected | |
| Control | 5.0 |
| SM-1213 | 5.0 |
| Infected | |
| No drug | 2.0 |
| SM-1213 | 5.5 |

These data illustrate that virus-induced immunodepression of the humoral type can be reversed by treatment with SM-1213. Complications of viral disease include immunodepression, which can contribute to the development of secondary infections by bacteria and other viruses.

The above procedures may be carried out employing SM-1211 with essentially the same results.

EXAMPLE XVI

Well-established methodology of the prior art was employed to determine the enhancement of the depressed humoral immune response system by SM-1213. The procedure described in Example XII was employed, except that paw swelling was evaluated at 4 hours following challenge. Four-hour swelling reflects the Arthus response and is dependent upon circulating antibody and complement for its generation. The results are presented in Table V. Note that, in similar mice, complement levels are not altered.

TABLE V

|  | 4 Hour Paw Swelling | |
|---|---|---|
|  | 12 Mice/Cage (mm × $10^{-2}$) | 2 Mice/Cage (mm × $10^{-2}$) |
| Day 28 challenge |  |  |
| Control | 95 ± 8 | 26 ± 3 |
| SM-1213 |  | 81 ± 12 |

These data indicate that treatment with SM-1213 enhances depressed humoral immune responses when depression results from psychosocial input. The significance of such results lies in the fact that the stress of psychosocial input that is associated with immunodepression is also linked with greater vulnerability to infectious and neoplastic disease.

The above procedure may be carried out employing SM-1211 with essentially the same results.

EXAMPLE XVII

Well-established methodology of the prior art is employed to determine the antiviral potency of SM-1211 and SM-1213 in a virus-infected mouse cell system employing stimulated macrophages and antiviral effectors. Note that macrophages have been observed to suppress the multiplication of both RNA and DNA enveloped and unenveloped viruses when these infect epithelial and connective tissue cells, that make up components of infected organs (Morahan, P. W. Glasgow, L. A., Crane, J. L., Jr., and Kern, E. R., *Cell. Immunol.* 28:404, 1977).

Peritoneal exudate cells (consisting mostly of macrophages) are harvested from mouse peritoneal cavities after being activated or elicited by prior injection of *Corynebacterium parvum* vaccine, vaccinia virus or glycogen. Glycogen stimulated mice are injected intraperitoneally with 0.5 ml 5 days prior to cell harvest. Mice receiving the bacterial vaccine are treated intraperitoneally with *C. parvum* (70 mg/kg) 7 or 14 days prior to macrophage harvest. Vaccinia "immune" macrophages are obtained from mice inoculated intraperitoneally with a non-lethal inoculum ($1 \times 10^5$ PFU) of vaccinia virus 14 days prior to cell harvest. Animals receiving SM-1211 or SM-1213 are given 4 or 0.4 mg/ml in their drinking water for the 2 days prior to harvest.

Mouse fibroblast cultures in 35 mm petri dish wells are infected with 20-50 PFU of either vaccinia virus, herpes simplex virus or EMC virus. After virus absorption at 36° C. for one hour, cells are washed with medium and macrophages in complete medium are added and allowed to attach for 2 hours at 36° C. Non-adherent (non-macrophage) cells are removed by three washings with phosphate-buffered saline, complete medium added and the plates incubated at 36° C. for 72 hours. At various intervals, pools of cell culture supernatant fluid from at least 2 cultures are obtained and frozen for subsequent assay of cell-free virus.

At 72 hours, in some experiments the monolayers are fixed with formalin and stained with methylene blue to determine the number of virus plaques. In other experiments cells are overlaid with complete medium containing 5% agarose and virus plaques visualized after addition of neutral red. The results indicate that, against the three viruses employed, treatment with SM-1211 and SM-1213 significantly reduces plaque formation and virus yield when added to all forms of macrophage elicitation employed.

EXAMPLE XVIII

The procedure described in Example XVII is employed, except that SM-1211 or SM-1213 is added to petri dish wells along with macrophages at a drug concentration of 1.0, 0.1 or 0.01 μg/ml. The results indicate that, against the three viruses employed, drug treatments significantly reduce plaque formation and virus yield when added to all forms of macrophage elicitation employed. The antiviral effects seem to be more profound than when drug is added only to mouse drinking water before macrophage harvest.

EXAMPLE XIX

Well-established methodology of the prior art was employed to determine the antiviral potency of SM-1213 in mice against vaccinia virus, a virus type known to be suppressed in large part by macrophage action (Morahan, P. W., Glasgow, L. A., Crane, J. L., Jr., and Kern, E. R., *Cell. Immunol.* 25:404, 1977).

In this study, 48 female CFW weanling mice (average weight 11.5 gm) were inoculated intravenously in a tail vein with 0.05 ml of a $3 \times 10^{-1}$ solution of stock virus. Beginning on day 5, after recording the appearance of typical tail pox and swelling, and continuing through day 10, half of the animals received distilled water by oral gavage, while half received 7 mg/kg SM-1213 by oral gavage one time daily.

Mice were examined for the development of tail lesions from day 5 through day 10, according to the method of Boyle et al (Boyle, J. J., Haff, R. F., and Stewart, R. C., *Antimicrob. Ag. Chemother.* 1966, American Society for Microbiology, 1967, pg. 536-539). In this evaluation, we considered the following discrete tail lesions:

1. The pox type, in which there appeared focal necrotic centers (as reported by Boyle et al),
2. Focal swellings that did not necessarily progress through pox formation, and
3. Deep necrosis with sunken areas of tissue degeneration and reabsorption, sometimes leading to spontaneous amputation of the tail. In our rating system, each pox, each focal swelling, and each millimeter of necrosis (including millimeters spontaneously amputated) was given a score of 1.

TABLE VI

|  | Control | Treated |
|---|---|---|
| Average Score for Tail Pox and Related Lesions | | |
| Day 5 | 0.75 ± 0.16 | 0.60 ± 0.14 |
| Treatment Initiation | | |
| Day 6 | 3.42 ± 0.74 | 0.83 ± 0.16[a] |
| 7 | 8.21 ± 1.22 | 2.60 ± 0.34[a] |
| 8 | 12.55 ± 2.10 | 3.72 ± 0.67[a] |
| 9 | 12.53 ± 2.01 | 5.00 ± 1.02[b] |
| 10 | 10.60 ± 2.24 | 3.00 ± 0.75[b] |
| Total pox days following treatment initiation | 47.00 ± 9.20 | 14.22 ± 2.75[a] |

[a] $p < 0.01$
[b] $p < 0.05$

These results illustrate that compounds of the invention exert a highly significant antiviral effect in vivo in an infection for which recovery is in large part macrophage dependent.

The above procedure may be carried out employing SM-1211 with essentially the same results.

I claim:

1. A method of enhancing microbicidal activity of phagocytes, including macrophages, in a warm blooded animal comprising administering to the animal in need thereof an amount effective to enhance said activity of a hexose monosaccharide ethereally substituted at the 3-position with a group of the formula $(CH_2)_nNR_2$ wherein n is 1, 2, 3 or 4 and R is hydrogen, methyl, ethyl, propyl or butyl; or a physiologically acceptable salt thereof.

2. The method of claim 1 wherein said hexose monosaccharide is further ethereally substituted at one or more positions with substituents selected from an alkyl of 1-5 carbon atoms, a group of the formula $(CH_2)_nNR_2$ or a blocking group.

3. The method of claim 2 wherein said hexose monosaccharide is glucose.

4. The method of claim 1 wherein said hexose monosaccharide is glucose.

5. The method of claim 4 wherein said group of the formula $(CH_2)_nNR_2$ is N',N'-dimethylamino-n-propyl.

6. The method of claim 3 wherein said group of the formula $(CH_2)_nNR_2$ is N',N'-dimethylamino-n-propyl.

7. The method of claim 1 wherein said group of the formula $(CH_2)_nNR_2$ is N',N'-dimethylamino-n-propyl.

8. The method of claim 6 wherein said hexose monosaccharide is 1,2-O-isopropylidene-3-O-3'-(N',N'-dimethylamino-n-propyl)-D-glucose.

9. The method of claim 5 wherein said hexose monosaccharide is 3-O-3'-(N',N'-dimethylamino-n-propyl)-D-glucose.

10. The method of claim 9 wherein said physiologically acceptable salt of said hexose monosaccharide is a hydrochloric acid salt.

11. The method of claim 8 wherein said physiologically acceptable salt of said hexose monosaccharide is a hydrochloric acid salt.

12. The method of claim 6 wherein said hexose monosaccharide is 1,2-O-isopropylidene-3-O-3'-(N',N'-dimethylamino-n-propyl)-alpha,D-glucose.

13. The method of claim 12 wherein said physiologically acceptable salt of said hexose monosaccharide is a hydrochloric acid salt.

* * * * *